United States Patent [19]
Matsuura et al.

[11] Patent Number: 5,658,924
[45] Date of Patent: Aug. 19, 1997

[54] 1,8-NAPHTHYRIDIN-2-ONE DERIVATIVE AND USE THEREOF

[75] Inventors: Akihiro Matsuura, Hamura; Naoki Ashizawa, Fussa; Takema Hase, Hamura, all of Japan

[73] Assignee: The Green Cross Corporation, Osaka, Japan

[21] Appl. No.: 448,408

[22] PCT Filed: Dec. 1, 1992

[86] PCT No.: PCT/JP92/01575

§ 371 Date: Jun. 1, 1995

§ 102(e) Date: Jun. 1, 1995

[87] PCT Pub. No.: WO94/12499

PCT Pub. Date: Jun. 9, 1994

[51] Int. Cl.$^6$ .................... A61K 31/44; A61K 31/56; A61K 31/505; C07D 470/04
[52] U.S. Cl. .................... 514/300; 514/254; 514/255; 514/256; 544/333; 544/336; 544/362; 544/405; 546/122
[58] Field of Search ............... 546/122; 514/300, 514/255, 256, 254; 544/238, 333, 336, 362, 405

[56] References Cited

U.S. PATENT DOCUMENTS 3,993,656  11/1976  Rooney .................... 260/296 N
4,735,948  4/1988   Wright .................... 514/299

OTHER PUBLICATIONS

Rubanyi GM; Botelho LH (1991) FASEB J, 5 (12) 2713–20. Sep. 1991.

*Primary Examiner*—C. Warren Ivy
*Assistant Examiner*—Evelyn Huang
*Attorney, Agent, or Firm*—Sughrue, Mion, Zinn, Macpeak & Seas

[57] ABSTRACT

The present invention relates to 1,8-naphthyridin-2-one derivatives, pharmaceutically acceptable acid addition salts and therapeutic agents comprising said compound as an active ingredient, which are used for the diseases such as circulatory diseases and respiratory diseases (e.g. hypertension, renal failure, heart failure, angina pectoris, myocardial infarction, arteriosclerosis, romsoongiitis obliterans, aortitis syndrome, bronchial asthma and peripheral diseases such as peripheral circulatory disorders), central nervous system diseases (e.g. depression, degradatior of central nervous function after cerebrovascular obliteration, cerebrovascular dementia, senile dementia, Alzheimer dementia and memory learning function disorders), various inflammations, and obesity.

9 Claims, No Drawings

1,8-NAPHTHYRIDIN-2-ONE DERIVATIVE AND USE THEREOF

TECHNICAL FIELD

This application is the national phase of ACT/JP92/01575 filed Dec. 1, 1992.

The present invention relates to 1,8-naphthyridin-2-one derivatives, pharmaceutically acceptable acid addition salts and therapeutic agents for the diseases such as peripheral diseases (e.g. hypertension, renal failure, heart failure, angina pectoris, myocardial infarction and peripheral circulatory disorders), circulatory diseases and respiratory diseases (e.g. arteriosclerosis, romsoongiitis obliterans, aortitis syndrome and bronchial asthma), central nervous system diseases (e.g. depression, degradation of central nervous function after cerebrovascular obliteration, cerebrovascular dementia, senile dementia, Alzheimer dementia and memory learning function disorders), various inflammations, and obesity, which comprise said compound as an active ingredient.

BACKGROUND ART (1) An endothelin is a strong vasoconstrictive peptide derived from endotheliocytes, which consists of 21 amino acids, and was isolated and identified by Yanagisawa et al in 1988 [M. Yanagisawa et al., Nature 332, 411 (1988)]. The vasoconstriction by endothelin is stronger than that by known vasoconstrictive substances such as angiotensin II, vasopressin and neuropeptide Y. Although the constriction is moderate, it lasts for a long time. Endothelin also shows contractive action on various blood vessels inclusive of microvessels of various animals.

The contraction by endothelin is not affected by receptor antagonists and synthesis inhibitors of known blood vessel agonists, such as norepinephrine, histamine, acetylcholine, serotonin, leukotriene and thromboxane $A_2$, and is known to be only suppressed by potential-dependent calcium channel antagonists and endotheline receptor antagonistic substances.

It is also known that endothelin induces not only vasoconstriction, but also strong airway stenosis [Y. Uchida et al., Eur. J. Pharmacol. 154, 227 (1988)]. It has been gradually clarified that endothelin has various physiological actions such as promotion of release of atrial sodium diuretic hormone in cultured atrial muscle of rats and suppression of renin secretion in pararenal glomerular cells.

Although its action in the living body and pathological involvement have not been entirely elucidated, endothelin is considered to be involved in various diseases, in view f the wide distribution of endothelin receptors and a variety of actions it shows. In fact, the involvement of endothelin has been pointed out in various diseases and experimental animal models. To be specific, patients and pathological animal models with pulmonary hypertension [D. J. Stewart et. al., Am. Col. Physic. 114, 464 (1991)], renal failure [M. Shichiri et al., Hypertension 15, 493 (1990)], heart failure [K. B. Margulies, Circulation 82, 2226 (1990)], angina pectoris [T. Toyo-oka et al., Circulation 83, 476 (1991)], myocardial infarction [Lancet Jul. 1, 53 (1989)], ischemic brain, peripheral diseases, arteriosclerosis, romsoongitis obliterans (Bueger's disease), aortitis syndrome (Takayasu's disease) [JAMA, 264, 2868 (1990)] or bronchial asthma show increased endothelin level in plasma, thus suggesting the possibility of endothelin being deeply involved in the onset and cause, retention and progress of the diseases.

(2) A cyclic adenosine monophosphate (cAMP) and cyclic guanosine monophosphate (cGMP), which are tntracellular second messengers, are decomposed and inactivated by phosphodiesterase (PDE). It has been known that PDE is widely distributed in the tissues in the body, and that PDE inhibitors provide various pharmacological actions by increasing cAMP and cGMP levels in the cells by inhibiting PDE. For example, they provide relaxing action in vascular smooth muscles and tracheal smooth muscles, as well as positive inotropic action and chronotropic action in the heart. They also control the central nervous function caused by increased cAMP in the central nervous system; namely, they show antidepression and memory learning function-improving action. Besides these, they show blood platelets coagulation-suppressive action, suppressive action on the activation of inflammatory cells, and lipolytic action in fat tissues [C. D. Nicholson et al., Trends in Pharmacol. Sci., 12, 19 (1991)].

Accordingly, the provision of, (1) a compound effective for the prophylaxis and treatment of various circulatory diseases and respiratory diseases such as hypertension, renal failure, heart failure, angina pectoris, myocardial infarction, ischemic brain-peripheral diseases, arteriosclerosis, romsoongiitis obliterans, aortitis syndrome and bronchial asthma, which are caused by abnormal regulation of various biological actions mediated by endothelin, a kind of autacoid produced in the body, by suppressing such physiological actions, and (2) a compound effective as a therapeutic agent for various diseases such as heart failure, thrombosis, depression, degradation of central nervous function after cerebrovascular obliteration, cerebrovascular dementia, senile dementia, Alzheimer dementia, bronchial asthma, various inflammations and obesity, which suppresses PDE, have been desired.

DISCLOSURE OF THE INVENTION

In view of the above-mentioned situation the present inventors have found that a series of 1,8-naphthyridin-2-one derivatives suppress various actions of endothelin; that is, while it has been known that an intravenous administration of endothelin in a high dose causes death of mice [Z. Terashita et al., Life Sci. 45, 1911 (1989)], an administratipn of a 1,8-naphthyridin-2-one derivative in advance markedly suppresses such effect; and that 1,8-naphthyridin-2-one-derivatives are effective for the prophylaxis and treatment of pressor activity by endothelin in rats, and suppress vasoconstriction in extracted pig coronary artery, which was caused by the addition of endothelin, and contraction in extracted guinea pig bronchial specimen, which was caused by other contractor drugs (e.g. histamine and leukotriene $D_4$); and that 1,8-naphthyridin-2-one derivatives show PDE inhibitory action, namely, that the compound of the present invention has a potent inhibitory action on the PDE separated and purified from the ventricular muscle of pig heart, which resulted in the completion of the invention.

BEST MODE FOR EMBODYING THE INVENTION

The present invention relates to 1,8-naphthyridin-2-one derivatives of the formula (I)

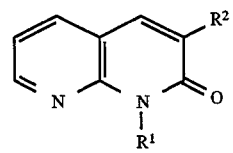

wherein $R^1$ is an optionally substituted alkyl or alkenyl, and $R^2$ is an optionally substituted aryl or 5- or 6-membered hetero ring, pharmaceutically acceptable acid addition salts and therapeutic agents comprising said compound as an active ingredient, which are used for the diseases such as circulatory diseases and respiratory diseases (e.g. hypertension, renal failure, heart failure, angina pectoris, myocardial infarction, arteriosclerosis, romsoongiitis obliterans, aortitis syndrome, bronchial asthma and peripheral diseases such as peripheral circulatory disorders), central nervous system diseases (e.g. depression, degradation of central nervous function after cerebrovascular obliteration, cerebrovascular dementia, senile dementia, Alzheimer dementia and memory learning function disorders), various inflammations, and obesity.

In the present Specification, alkyl means linear or branched alkyl having 1 to 6 carbon atoms, such as methyl, ethyl, propyl, isopropyl, butyl, isobutyl, sec-butyl, tert-butyl, pentyl, isopentyl, sec-pentyl, tert-pentyl, hexyl, isohexyl, sec-hexyl and tert-hexyl, with preference given to methyl and tert-butyl.

These alkyl groups may be substituted by various substituents such as halogen atom, cycloalkyl and optionally substituted aryl. Examples of the substituents include halogen atoms such as fluorine and chlorine, cycloalkyl such as cyclopropyl and aryl (e.g. phenyl optionally substituted by halogen atom etc.).

Alkenyl is exemplified by vinyl, allyl, butenyl and pentenyl.

Aryl is exemplified by phenyl and naphthyl, which may be substituted by alkyl, alkoxy or halogen atom. The alkyl here is as defined above, and alkoxy is that derived from said alkyl. Examples thereof include phenyl substituted by methyl, methoxy, chlorine and the like.

The 5- or 6-membered hetero ring means a hetero ring having one or more of oxygen atom, sulfur atom and nitrogen atom, and is exemplified by thiophene, furan, pyrrole, imidazole, pyrazole, isothiazole, isoxazole, pyrrolidine, imidazolidine, pyridine, pyrazine, pyrimidine, pyridazine, piperidine and piperazine. These groups may be substituted by alkyl, halogen atom and the like. Preferred is a 6-membered hetero ring having one or more nitrogen atoms, with most preference given to pyridine and piperidine.

The representative compounds of the present invention are shown in the following Tables 1 to 11, wherein $R^1$ and $R^2$ are those in the aforementioned formula (I).

TABLE 1

| $R^1$ | $R^2$ |
| --- | --- |
| —CH₃ |  |
| —CH₃ | 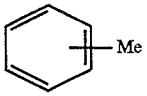 |
| —CH₃ | 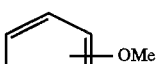 |
| —CH₃ | 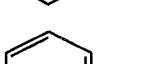 |

TABLE 1-continued

| $R^1$ | $R^2$ |
| --- | --- |
| —CH₃ | 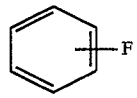 |
| —CH₃ | 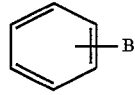 |
| —CH₃ |  |
| —CH₃ |  |
| —CH₃ |  |

TABLE 2

| $R^1$ | $R^2$ |
| --- | --- |
| —CH₂— | 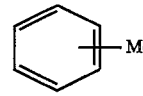 |
| —CH₂— | 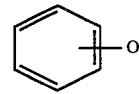 |
| —CH₂— | 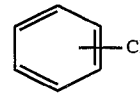 |
| —CH₂— | 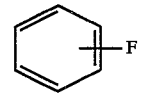 |
| —CH₂— |  |
| —CH₂— |  |
| —CH₂— |  |
| —CH₂— |  |

TABLE 2-continued
| R¹ | R² |
|---|---|
| 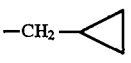 | 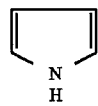 |
TABLE 3
| R¹ | R² |
|---|---|
| 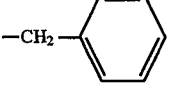 | 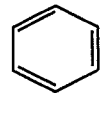 |
| 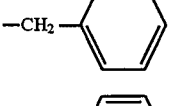 | 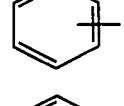 |
| 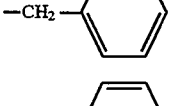 | 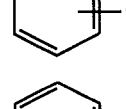 |
| 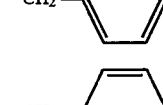 | 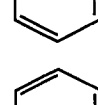 |
| 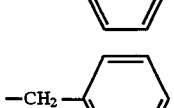 | 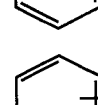 |
| 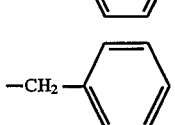 |  |
| 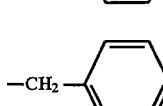 | 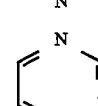 |
| 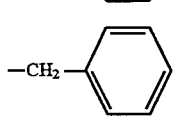 | 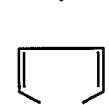 |
| 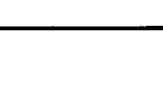 | 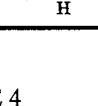 |
TABLE 4
| R¹ | R² |
|---|---|
| 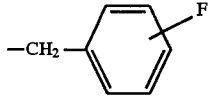 |  |
TABLE 4-continued
| R¹ | R² |
|---|---|
| 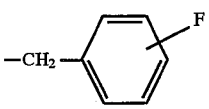 | 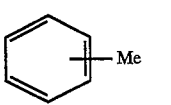 |
| 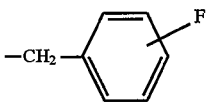 | 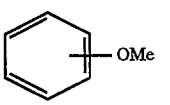 |
| 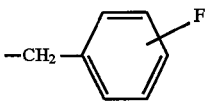 | 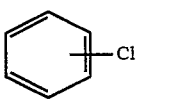 |
| 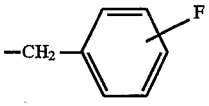 | 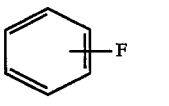 |
| 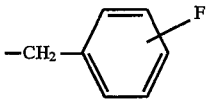 | 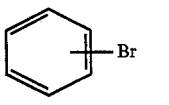 |
| 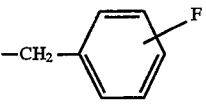 | 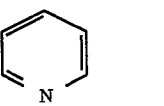 |
| 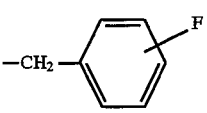 | 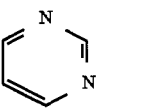 |
| 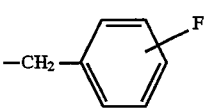 | 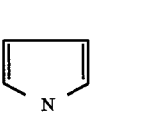 |
TABLE 5
| R¹ | R² |
|---|---|
| —(CH$_2$)$_3$—CH$_3$ |  |
| —(CH$_2$)$_3$—CH$_3$ |  |
| —(CH$_2$)$_3$—CH$_3$ |  |
| —(CH$_2$)$_3$—CH$_3$ |  |

TABLE 5-continued

| R¹ | R² |
|---|---|
| $-(CH_2)_3-CH_3$ | phenyl-F |
| $-(CH_2)_3-CH_3$ | phenyl-Br |
| $-(CH_2)_3-CH_3$ | pyridine (N) |
| $-(CH_2)_3-CH_3$ | pyrimidine (N,N) |
| $-(CH_2)_3-CH_3$ | pyrrole (NH) |

TABLE 6

| R¹ | R² |
|---|---|
| $-(CH_2)_2-CH(CH_3)_2$ | phenyl |
| $-(CH_2)_2-CH(CH_3)_2$ | phenyl-Me |
| $-(CH_2)_2-CH(CH_3)_2$ | phenyl-OMe |
| $-(CH_2)_2-CH(CH_3)_2$ | phenyl-Cl |
| $-(CH_2)_2-CH(CH_3)_2$ | phenyl-F |
| $-(CH_2)_2-CH(CH_3)_2$ | phenyl-Br |
| $-(CH_2)_2-CH(CH_3)_2$ | pyridine (N) |
| $-(CH_2)_2-CH(CH_3)_2$ | pyrimidine (N,N) |

TABLE 6-continued

| R¹ | R² |
|---|---|
| $-(CH_2)_2-CH(CH_3)_2$ | pyrrole (NH) |

TABLE 7

| R¹ | R² |
|---|---|
| $-(CH_2)_4-CH_3$ | phenyl |
| $-(CH_2)_4-CH_3$ | phenyl-Me |
| $-(CH_2)_4-CH_3$ | phenyl-OMe |
| $-(CH_2)_4-CH_3$ | phenyl-Cl |
| $-(CH_2)_4-CH_3$ | phenyl-F |
| $-(CH_2)_4-CH_3$ | phenyl-Br |
| $-(CH_2)_4-CH_3$ | pyridine (N) |
| $-(CH_2)_4-CH_3$ | pyrimidine (N,N) |
| $-(CH_2)_4-CH_3$ | pyrrole (NH) |

TABLE 8

| R¹ | R² |
|---|---|
| $-(CH_2)_3-CH(CH_3)_2$ | phenyl |
| $-(CH_2)_3-CH(CH_3)_2$ | phenyl-Me |

TABLE 8-continued

| R¹ | R² |
|---|---|
| −(CH₂)₃−CH(CH₃)₂ | phenyl-OMe |
| −(CH₂)₃−CH(CH₃)₂ | phenyl-Cl |
| −(CH₂)₃−CH(CH₃)₂ | phenyl-F |
| −(CH₂)₃−CH(CH₃)₂ | phenyl-Br |
| −(CH₂)₃−CH(CH₃)₂ | pyridyl |
| −(CH₂)₃−CH(CH₃)₂ | pyrimidyl |
| −(CH₂)₃−CH(CH₃)₂ | pyrrolyl (NH) |

TABLE 9

| R¹ | R² |
|---|---|
| −CH₂CH=CH₂ | phenyl |
| −CH₂CH=CH₂ | phenyl-Me |
| −CH₂CH=CH₂ | phenyl-OMe |
| −CH₂CH=CH₂ | phenyl-Cl |
| −CH₂CH=CH₂ | phenyl-F |
| −CH₂CH=CH₂ | phenyl-Br |
| −CH₂CH=CH₂ | pyridyl |
| −CH₂CH=CH₂ | pyrimidyl |
| −CH₂CH=CH₂ | pyrrolyl (NH) |

TABLE 10

| R¹ | R² |
|---|---|
| −CH=CHCH₃ | phenyl |
| −CH=CHCH₃ | phenyl-Me |
| −CH=CHCH₃ | phenyl-OMe |
| −CH=CHCH₃ | phenyl-Cl |
| −CH=CHCH₃ | phenyl-F |
| −CH=CHCH₃ | phenyl-Br |
| −CH=CHCH₃ | pyridyl |
| −CH=CHCH₃ | pyrimidyl |
| −CH=CHCH₃ | pyrrolyl (NH) |

TABLE 11

| R¹ | R² |
|---|---|
| —CH=CH₂ | phenyl |
| —CH=CH₂ | 4-methylphenyl (Me) |
| —CH=CH₂ | 4-methoxyphenyl (OMe) |
| —CH=CH₂ | 4-chlorophenyl (Cl) |
| —CH=CH₂ | 4-fluorophenyl (F) |
| —CH=CH₂ | 4-bromophenyl (Br) |
| —CH=CH₂ | pyridyl |
| —CH=CH₂ | pyrazinyl |
| —CH=CH₂ | pyrrolyl (NH) |

The pharmaceutically acceptable acid addition salts include salts with inorganic acid such as hydrochloric acid, sulfuric acid, nitric acid and phosphoric acid, and salts with organic acid such as acetic acid, formic acid, propionic acid, succinic acid, fumaric acid, maleic acid, tartaric acid and citric acid.

The compound of the present invention can be administered orally or parenterlly. When an oral administration is desired, the compound of the present invention can be used as a conventional pharmaceutical preparation in the dosage form such as solid preparation (e.g. tablet, powder, capsule and granule) and liquid preparation (e.g. aqueous or oily suspension, syrup and elixir). When a parenteral administration is desired the compound of the present invention can be used in the form of an aqueous or oily suspension for injection. For the preparation thereof, conventional excipients, binders, lubricants, aqueous solvents, oily solvents, emulsifiers, suspending agents and the like can be used as appropriate. Other additives such as preservatives and stabilizers can be also added.

While the dose of the compound of the present invention varies depending on the administration route, age, body weight and condition of patients, and the kind of disease, it is generally 1–300 mg, preferably 10–100 mg, daily by oral administration and 1–200 mg, preferably 5–50 mg, daily by parenteral administration, which are administered in 1 to 5 doses.

EXAMPLES

The present invention is described in more detail by Examples and Experimental Examples given in the following, to which the present invention is not limited.

Example 1

[Compound 1]

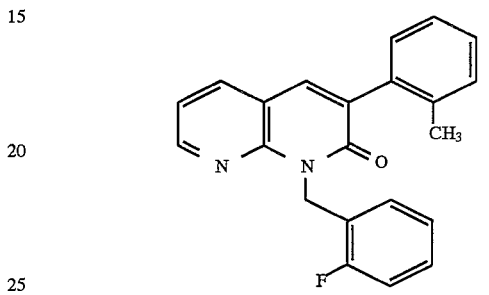

Oily sodium hydride (100 mg, content 55%) was washed with dry hexane under a dry argon atmosphere, and suspended in dry N,N-dimethylformamide (4 ml). Ethyl o-tolyl acetate (348 mg) was dropwise added under ice-cooling. The mixture was stirred for 30 minutes, and dry N,N-dimethylformamide (1 ml) containing 2-aminonicotinaldehyde (200 mg) was dropwise added. The mixture was stirred for 2 hours at room temperature, and dry N,N-dimethylformamide (1 ml) containing o-fluorobenzyl bromide (310 mg) was dropwise added. The mixture was stirred for 3 hours at room temperature, and water (10 ml) was added. The mixture was extracted three times with chloroform. The organic layers thus extracted were combined, washed 4 times with water and once with saturated brine, and dried over anhydrous sodium sulfate.

The solvent was distilled away under reduced pressure from the organic layer to give 950 mg of the residue. The residue was subjected to silica gel column chromatography and the fraction eluted in benzene was recrystallized from toluene to give 130 mg of 1-(2-fluorobenzyl)-3-(2-methylphenyl)-1,8-naphthyridin-2(1H)-one (Compound 1), Rf value: 0.60, toluene: ethyl acetate=4:1. The physico-chemical data of the product are given below.

$^1$H-NMR(CDCl$_3$) δ (ppm): 2.24 (3H,S), 5.89 (2H, S), 6.92–7.29 (9H,m), 7.65 (1H,S), 7.88 (1H,dd,J=1.95 Hz,4.88 Hz), 8.55 (1H,dd,J=1.95 Hz,7.81 Hz)

$^{13}$C-NMR(CDCl$_3$) δ (ppm): 19.95, 38.77, 115.09, 115.31, 115.59, 118.33, 123.77, 123.80, 124.64, 124.79, 125.65, 128.25, 128.33, 128.38, 129.77, 130.08, 135.55, 136.06, 136.24, 136.93, 149.43, 149.67, 159.56, 161.64, 162.01

MS(CI)m/z: 345(MH$^+$)

Examples 2–5

By reacting the corresponding compounds as starting materials in the same manner as in Example 1, the following compounds 2 to 5 were obtained.

TABLE 12

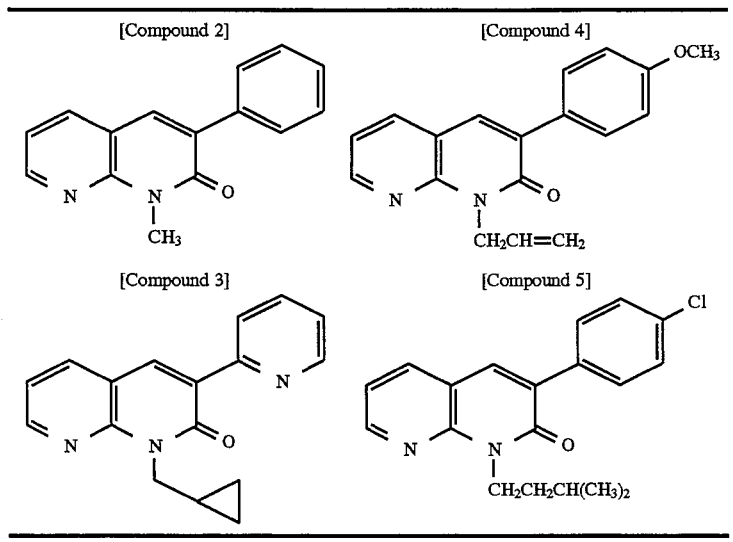

The formulation examples in the present invention are shown in the following.

Formulation Example 1

Tablet: The compound (Compound 1, 0.5 part by weight) of Example 1 and lactose (4.5 parts by weight) were mixed and pulverized, and lactose (48 parts by weight), crystalline cellulose (22.5 parts by weight) and magnesium stearate (0.4 part by weight) were added to the mixture, and the mixture was homogeneously mixed. The mixture was pressure-formed by a compressor to give tablets (75 mg/tablet).

Formulation Example 2

Capsule: The compound (Compound 1, 0.5 part by weight) of Example 1 and lactose (4.5 parts by weight) were mixed and pulverized, and lactose (14.5 parts by weight), corn starch (60.0 parts by weight) and magnesium stearate (2.0 parts by weight) were added to the mixture. The mixture was homogeneously mixed. The mixture was filled in gelatin hard capsules (No. 3) by 200 mg per capsule to give capsules.

Experimental Examples

That the 1,8-naphthyridin-2-one derivatives are effective agents for the prophylaxis and treatment of high endothelin diseases, that they are suppressive drugs for bronchial smooth muscle contraction caused by other stimulants, and that they are PDE inhibitors are explained in detail by way of the Experimental Examples in the following. The similar effects were found with regard to the compounds not exemplified here.

Experimental Example 1

Prevention of lethal effect on mice induced by intravenous administration of endothelin (Method)

Male ICR mice (6–7 weeks of age) were used without anesthetization. A solvent (physiological saline or 0.5% carboxymethylcellulose in physiological saline) or a medium, in which a drug had been dissolved or suspended, was administered in a dose of 50 μl /10 g body weight via the tail vein of the mice. Five minutes later, 5 nmol/kg of endothelin (Peptide Institute) dissolved in the same amount of a solvent was intravenously administered. The mice were monitored for 60 minutes after the endothelin administration and the number of dead animals and the latency (seconds) until death were determined. The latency of the animal that did not die in 60 minutes from the endothelin administration was taken as 3600 seconds. The test results of Compound 2 are representatively shown.

(Test results)

The test results are shown in Table 13. Compound 2 showed suppression of the death caused by endothelin and a prolonging action of the latency until death.

TABLE 13

Prevention, by 1,8-naphthyridin-2-one derivative, of endothelin-induced lethal effect on mice

| Administered | Dose mg/kg i.v. | Prevention of death | |
| --- | --- | --- | --- |
| | | suppression of death (%) | prolongation of latency (%) |
| Compound 2 | 30 | 52 | 305** |

Determination of significant difference: Tukey's multiple comparison method relative to control group: ** P<0.01

Experimental Example 2

Effect against endothelin-induced pressor activity in rats (Method)

Male SD rats (6 to 8 weeks of age) were anesthetized with sodium pentobarbital (60 mg/kg, i.p.), and a polyethylene catheter was inserted in the left carotid artery, which was connected to a pressure transducer (TP-400T, manufactured by Nihon Koden), and the blood pressure was measured via a polygraph (RM-6000 manufactured by Nihon Koden).

The pressor activity was induced by administering endothelin (1 nmol/kg) dissolved in a solvent, from the femoral vein. With regard to the animals ascertained to have increased blood pressure, a solvent or a medium, in which a drug had been dissolved or suspended, was administered in a dose of 1 ml/kg from the femoral vein of the rats 10 minutes after the endothelin administration, and the pressor activity was observed thereafter. The representative test results of Compound 2 are shown.
(Test results)

The results are shown in Table 14. in the Table, changes in blood pressure 20 minutes after the endothelin administration was compared with the value obtained before the endothelin administration.

TABLE 14

Effect of 1,8-naphthyridin-2-one derivative against pressor activity caused by endothelin in rats

| Administered | Dose mg/kg i.v. | Endothelin-induced pressor activity Suppression % |
|---|---|---|
| Compound 2 | 10 | 38.5 |

Experimental Example 3

Suppression of endothelin-induced contraction in extracted pig coronary artery (Method)

Rectangular specimens of pig left anterior descendens coronary artery (endothelial cells removed) were used. The specimens were heated to 37° C. and suspended in a Tyrode's solution (10 ml) aerated with a 95% $O_2$–5% $CO_2$ mixed gas under the resting tension of 1.5 g, and changes in isometric tension were determined. The specimens were contracted with 10 nM endothelin and when the reaction became stable, a drug dissolved in dimethyl sulfoxide was added to the. Tyrode's solution. The relaxation ratio was calculated relative to the base line before the contraction, which was taken as 100% relaxation. The representative test results of Compound 2 (administration concentration: 10 μM) are shown.
(Test results)

The results are shown in Table 15. Compound 2 showed evident suppressive action on the endothelin-induced contraction of extracted pig coronary artery specimens.

TABLE 15

Suppression, by 1,8-naphthyridin-2-one derivative, of endothelin-induced contraction of extracted pig coronary artery specimen

| Administered | Concentration | Suppression % |
|---|---|---|
| Compound 2 | 10 μM | 74 |

Experimental Example 4

Suppression of histamine or leukotriene $D_4$-induced contraction of bronchial specimen extracted from guinea pig (Method)

Male Hartley guinea pigs weighing 250–450 g were fainted by hitting in the head and exsanguinated to death. The trachea was removed and ring specimens were prepared by a conventional method. The specimens were kept at 37° C. and suspended in a Krebs-Ringer solution (10 ml) aerated with a 95% $O_2$–5% $CO_2$ mixed gas, and isometric tension was measured. The specimens were contracted with histamine (3 μM) or leukotriene $D_4$ (1 nM). When the reaction became stable, a drug dissolved in dimethyl sulfoxide was added to the Kreb's Ringer solution. The relaxation ratio was calculated based on the base line before the contraction, which was taken as 100% relaxation.
(Test results)

The results are shown in Table 16.

TABLE 16

Suppression, by 1,8-naphthyridin-2-one derivative, of contraction of bronchial specimen extracted from guinea pig, which is caused by various contractors

| Administered | Concentration μM | Supression of contraction % | |
|---|---|---|---|
| | | HS | LT |
| Compound 1 | 10 | 100 | 88 |
| Compound 2 | 10 | 93 | — |
| Compound 3 | 1 | 60 | 100 |
| Compound 4 | 10 | 100 | 100 |

In the Table, HS means histamine-induced contraction, LT means leukotriene $D_4$-induced contraction and—means no test examples.

Experimental Example 5

Inhibition of PDE by 1,8-naphthyridin-2-one derivative (Method)

The centrifugation supernatant of the homogenate of pig ventricular muscle was separated into isozyme by ortho-(diethylaminoethyl)-cellulose chromatography and used as an enzyme source. Respective isozymes were confirmed by the reaction with respective activity regulators. [$^3$H]-cAMP was used as a substrate and the reaction was carried out in the presence of 5'-nucleotidase. A sample was dissolved in dimethyl sulfoxide and added to the reaction mixture. [$^3$H]-5'-AMP produced by PDE was decomposed into [$^3$H]-adenosine by 5'-nucleotidase. An anion exchange resin was added to adsorb the unreacted [$^3$H]-cAMP, whereby the reaction was stopped. The [$^3$H]-adenosine radioactivity of the supernatant was determined, based on which the PDE inhibitory action was calculated.
(Test results)

The results are shown in Table 17. Every compound selectively inhibited PDEIV.

TABLE 17

Inhibition of PDE by 1,8-naphthyridin-2-one derivative

| | PDE Inhibitory activity (IC$_5$:μM) PDE isozyme | | | |
|---|---|---|---|---|
| | I | II | III | IV |
| Compound 1 | >50 | >50 | >50 | 0.4 |
| Compound 2 | 29 | 39 | >50 | 1.6 |
| Compound 3 | 66 | 18 | 80 | 1.4 |
| Compound 4 | 49 | >50 | 44 | 0.38 |
| Compound 5 | >50 | >50 | >50 | 0.35 |

Experimental Example 6

Acute toxicity of 1,8-naphthyridin-2-one derivative in mice (Method)

ICR mice (6–8 weeks of age, 7 per group) were fasted overnight and used for the experiment. A solvent (0.5% aqueous solution of carboxymethylcellulose) or a medium, in which a drug had been dissolved or suspended, was orally administered to mice in a dose of 0.1 ml/10 g body weight, and life or death of the animals was monitored for 72 hours after the administration. The representative test results of Compound 2 (300 mg/kg p.o.) are shown.
(Test results)

The results are shown in Table 18. Compound 2 tested negative in the acute toxicity test in the dose of 300 mg/kg. Based on the results, oral lethal dose 50% ($LD_{50}$) was estimated to be not less than 300 mg/kg.

TABLE 18

Acute toxicity of 1,8-naphthyridin-2-one derivative in mice

| Administered | Number of animal administered | Death |
| --- | --- | --- |
| Compound 2 | 7 | 0 |

From the foregoing, it has been concluded that the compound of the present invention is useful as an effective drug for the prophylaxis and treatment of high endothelin diseases, as a suppressive drug for the contraction of bronchial smooth muscle caused by other stimulants and as a PDE inhibitor, and that the compound is highly safe.

Industrial Applicability 1,8-Naphthyridin-2-one derivatives and pharmaceutically acceptable salts thereof of the present invention are useful as therapeutic agents for the diseases such as circulatory diseases and respiratory diseases (e.g. hypertension, renal failure, heart failure, angina pectoris, myocardial infarction, arteriosclerosis, romsoongiitis obliterans, aortitis syndrome, bronchial asthma and periphral diseases such as peripheral circulatory disorders), central nervous system diseases (e.g. depression, degradation of central nervous function after cerebrovascular obliteration, cerebrovascular dementia, senile dementia, Alzheimer dementia and memory learning function disorders), various inflammations, and obesity.

What is claimed is:

1. A 1,8-naphthyridin-2-one derivative of the formula (I):

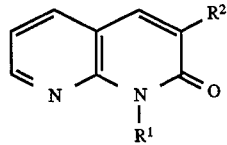

wherein
$R^1$ is an optionally substituted alkyl or alkenyl, and
$R^2$ is an optionally substituted aryl or 5- or 6-membered hetero ring selected from the group consisting of thiophene, furan, pyrrole, imidazole, pyrazole, isothiazole, isoxazole, pyrrilidine, imidazolidine, pyridine, pyrazine, pyrimidine, pyridazine, piperidine and piperazine, provided that $R^1$ is not a non-substituted ethyl and $R^2$ is not a non-substituted phenyl at the same time,
or a pharmaceutically acceptable acid addition salt thereof.

2. A pharmaceutical composition which comprises, as an active ingredient, an effective amount of 1,8-naphthyridin-2-one derivative of the formula (I)

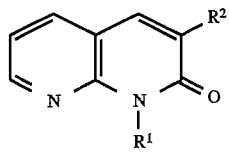

wherein $R^1$ is an optionally substituted alkyl or alkenyl, and $R^2$ is an optionally substituted aryl or a 5- or 6-membered hetero ring selected from the group consisting of thiophene, furan, pyrrole, imidazole, pyrazole, isothiazole, isoxazole, pyrrolidine, imidazolidine, pyridine, pyrazine, pyrimidine, pyridazine, piperidine and piperazine, or a pharmaceutically acceptable acid addition salt thereof and a pharmaceutically acceptable carrier.

3. The pharmaceutical composition of claim 2, wherein the alkyl represented by $R^1$ in the formula (I) is substituted by aryl or cycloalkyl.

4. The pharmaceutical composition of claim 2, wherein the aryl is a substituted phenyl.

5. The pharmaceutical composition of claim 2, wherein the hetero ring represented by $R^2$ in the formula (I) is a 6-membered ring having one or more nitrogen atoms selected from the group consisting of pyridine, pyrazine, pyrimidine, pyridazine, piperidine and piperazine.

6. The 1,8-naphthyridin-2-one derivative of claim 1, wherein the alkyl represented by $R^1$ in the formula (I) is substituted by aryl or cycloalkyl.

7. The 1,8-naphthyridin-2-one derivative of claim 1, wherein the aryl represented by $R^2$ in the formula (I) is a substituted phenyl.

8. The 1,8-naphthyridin-2-one derivative of claim 1, wherein the hetero ring represented by $R^2$ in the formula (I) is a 6-membered ring having one or more nitrogen atoms selected from the group consisting of pyridine, pyrazine, pyrimidine, pyridazine, piperidine and piperazine.

9. A method for inhibiting an activity of phosphodiesterase, in a mammal, comprising administering to mammal an amount effective for inhibiting an activity of phosphodieterase IV of a 1,8-naphthyridin-2-one derivative of the formula (I)

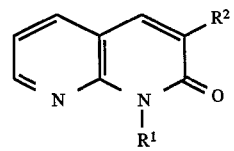

wherein $R^1$ is an otionally substituted alkyl or alkenyl, and $R^2$ is an optionally substituted aryl or 5- or 6-membered hetero ring selected from the group consisting of thiophen, furan, pyrrole, imidazole pyrazole, isothiazole, isoxazole, pyrrolidine, imidazolidine, pyridine, pyrazine, pyrimidine, pyridazine, piperidine and piperazine, or a pharmaceutically acceptable acid addition salt thereof.

* * * * *